US011141110B2

(12) United States Patent
Misaki

(10) Patent No.: US 11,141,110 B2
(45) Date of Patent: Oct. 12, 2021

(54) BODY MOVEMENT DETECTION SENSOR

(71) Applicant: ARK LIMITED LIABILITY COMPANY, Mitoyo (JP)

(72) Inventor: Yukinori Misaki, Kagawa (JP)

(73) Assignee: ARK LIMITED LIABILITY COMPANY, Kagawa (JP)

( * ) Notice: Subject to any disclaimer, the term of this patent is extended or adjusted under 35 U.S.C. 154(b) by 283 days.

(21) Appl. No.: 16/331,527

(22) PCT Filed: Sep. 5, 2017

(86) PCT No.: PCT/JP2017/031972
§ 371 (c)(1),
(2) Date: Mar. 8, 2019

(87) PCT Pub. No.: WO2018/047825
PCT Pub. Date: Mar. 15, 2018

(65) Prior Publication Data
US 2019/0200929 A1 Jul. 4, 2019

(30) Foreign Application Priority Data
Sep. 9, 2016 (JP) .............................. JP2016-176147

(51) Int. Cl.
*A61B 5/00* (2006.01)
*A61B 5/08* (2006.01)
(Continued)

(52) U.S. Cl.
CPC .......... *A61B 5/6823* (2013.01); *A61B 5/0245* (2013.01); *A61B 5/02438* (2013.01);
(Continued)

(58) Field of Classification Search
CPC ....... A61B 5/6823; A61B 5/0245; A61B 5/11; A61B 5/02438; A61B 5/1135; A61B 5/6831; A61B 5/08
(Continued)

(56) References Cited

U.S. PATENT DOCUMENTS

| 4,949,730 A | 8/1990 | Cobben et al. | |
| 2002/0123692 A1* | 9/2002 | Pail .................. | A63B 23/185 600/534 |

(Continued)

FOREIGN PATENT DOCUMENTS

| JP | S57-122844 | 7/1982 |
| JP | S63-501196 A | 5/1988 |

(Continued)

OTHER PUBLICATIONS

International Search Report in PCT Application No. PCT/JP2017/031972, dated Nov. 14, 2017, 4pp.
(Continued)

*Primary Examiner* — Amanda K Hulbert
*Assistant Examiner* — Philip C Edwards
(74) *Attorney, Agent, or Firm* — Hauptman Ham, LLP

(57) ABSTRACT

A body movement detection sensor includes a sensor section having a piezoelectric film, a right belt member, a left belt member, and an engagement member configured to engage the right and left belt members. In the body movement detection sensor, the piezoelectric film exhibits piezoelectric effect in a length direction, the right belt member and the left belt member have substantially no elasticity, the body movement detection sensor further includes an elastic sheet directly or indirectly connected to the right belt member and the left belt member, the piezoelectric film and the elastic sheet are arranged substantially without irregularities when viewed from a side, and the elastic sheet has a maximum (Continued)

amount of expansion larger than an amount of change of a thorax during breathing and has a length equal to or smaller than one-sixth of a total length of the right belt member and the left belt member.

6 Claims, 7 Drawing Sheets

(51) Int. Cl.
*A61B 5/0245* (2006.01)
*A61B 5/11* (2006.01)
*A61B 5/024* (2006.01)
*A61B 5/113* (2006.01)

(52) U.S. Cl.
CPC .................. *A61B 5/08* (2013.01); *A61B 5/11* (2013.01); *A61B 5/1135* (2013.01); *A61B 5/6831* (2013.01)

(58) Field of Classification Search
USPC ........................................................ 600/508
See application file for complete search history.

(56) References Cited

U.S. PATENT DOCUMENTS

| 2009/0259135 | A1* | 10/2009 | Stasz .................... A61B 5/7214 600/534 |
| 2010/0198084 | A1* | 8/2010 | Kim .................... A61B 5/02438 600/484 |
| 2014/0073970 | A1* | 3/2014 | Ashby .................. A61B 5/0833 600/484 |

FOREIGN PATENT DOCUMENTS

| JP | H1-92603 A | 4/1989 |
| JP | 4045344 B2 | 2/2008 |
| JP | 2009-172194 A | 8/2009 |
| JP | 2009-172197 A | 8/2009 |
| JP | 5299663 B2 | 9/2013 |
| WO | 02/069801 A1 | 9/2002 |

OTHER PUBLICATIONS

International Preliminary Report on Patentability in PCT Application No. PCT/JP2017/031972, dated Jul. 11, 2018, 12pp.
Yukinori Misaki, "A High Resolution PVDF (Piezoelectric) Film Respiration Sensor", National Institute of Technology, Japan Shin Gijutsu Setsumeikai Tojitsu Haifu Shiryo, Jul. 5, 2011, pp. 1 to 23, Kagawa Japan, 46pp.

* cited by examiner

BODY MOVEMENT DETECTION SENSOR

RELATED APPLICATIONS

The present application is a national phase of International Application Number PCT/JP2017/031972, filed Sep. 5, 2017, which claims priority to Japanese Application Number 2016-176147, filed Sep. 9, 2016.

TECHNICAL FIELD

The present invention relates to a body movement detection sensor using a piezoelectric film and an elastic sheet providing the piezoelectric film with variable tension.

BACKGROUND ART

Conventional body movement detection means are roughly classified into those that supply electric current through a sensor and measure electric resistance change and those that measure electric voltage change in a piezoelectric body caused by body movements.

The former body movement detection means include techniques of: measuring electric voltage change while a strain gauge (thin tube in which conductive material such as carbon particles is injected) wound on a body with electric current flowing through the strain gauge; and measuring inductance change of a coil sensor that is a thin conductive wire sewn to a band.

However, safety problems associated with electric current flowing around a body or problems of noise that affects other equipment have been pointed out. Additionally, in a case of a configuration that detects change in a resistance value by expansions and contractions of a conductive rubber sensor due to thorax volume change during breathing, there is an issue that pulling the conductive rubber sensor more strongly than a certain level results in irreversible change in characteristics of the conductive rubber sensor. Meanwhile, there is another issue that using the conductive rubber sensor within a range in which characteristics of the conductive rubber sensor do not change results in poor sensitivity.

The latter body movement detection means utilize a flexible film-shaped piezoelectric body since deflection has to be occurred in the piezoelectric body. As a piezoelectric film, Polyvinylidene fluoride film (PVDF) or piezoelectric ceramic or a piezoelectric ceramic thin film made of barium titanate, lead zirconate titanate (PZT), or the like is used. A method and apparatus of detecting delivery timing by monitoring muscular activity using PVDF has been proposed (Patent Literature 1).

As a body movement detection sensor suitable for detecting body movements, the inventor has proposed a body movement detection sensor that is configured with a piezoelectric film deflected in the shape of a bridge and an expansible member that is shorter than the piezoelectric film and that links both ends of the piezoelectric film, in which the deflection of the piezoelectric film changes in response to expansions and contractions of the expansible member in contact with a subject (Patent Literature 2).

The body movement detection sensor disclosed in Patent Literature 2, however, requires space for the deflection of the piezoelectric film in the shape of a bridge, which restricts size reduction.

Hence, the inventor have proposed a body movement detection sensor having a cover member that houses a piezoelectric film, a band member that is connected to the cover member and expands and contracts in the longitudinal direction along with body movements of the subject, a winding roll member, a locking roll member, and an elastic member locked by and wound on the winding roll member and the locking roll member, in which a first end portion of the piezoelectric film is wound around the winding roll member and a second end portion of the piezoelectric film is connected to an end portion of the band member. In the body movement detection sensor, rolling of the winding roll member causes the piezoelectric film to expand and contract and thereby electric voltage is generated (Patent Literature 3).

CITATION LIST

Patent Literatures

[Patent Literature 1] Japanese Examined Patent Publication No. S63-501196
[Patent Literature 2] Japanese Patent No. 4045344
[Patent Literature 3] Japanese Patent No. 5299663

SUMMARY

Technical Problem

Patent Literature 3 has made it possible to provide a body movement detection sensor of which piezoelectric film can be compactly housed in a cover member. However, since the body movement detection sensor is equipped with a winding roll member and a locking roll member, there has been structural limitations in reducing the thickness of the cover member.

In order to solve the issue, an object of the present invention is to provide a body movement detection sensor using a piezoelectric film, which improves detection accuracy and has a structure capable of achieving size reduction.

Solution to Problem

A body movement detection sensor of the present invention includes a sensor section having a piezoelectric film, a right belt member extending from a right side of the sensor section, a left belt member extending from a left side of the sensor section, and an engagement member for engaging an end portion of the right belt member and an open-end portion of the left belt member with each other. In the body movement detection sensor, the piezoelectric film exhibits piezoelectric effect in a length direction, the right belt member and the left belt member have substantially no elasticity, the body movement detection sensor further includes an elastic sheet directly or indirectly connected to the right belt member and the left belt member, the piezoelectric film and the elastic sheet are arranged substantially without irregularities when viewed from a side, and the elastic sheet has a maximum amount of expansion larger than an amount of change of a thorax during breathing and has a length equal to or smaller than one-sixth of a total length of the right belt member and the left belt member.

In the body movement detection sensor, the elastic sheet may have a maximum amount of expansion of 30 to 120 mm for adults, a maximum amount of expansion of 10 to 20 mm for infants, or a maximum amount of expansion of 20 to 60 mm for children.

The body movement detection sensor may further include a slide member that makes a length of the right belt member and/or the left belt member adjustable.

In the body movement detection sensor, the sensor section may include a case covering the piezoelectric film.

In the body movement detection sensor, the elastic sheet may be configured such that one end portion of the elastic sheet is slidable in the case.

In the body movement detection sensor, the elastic sheet may consist of a plurality of elastic sheets.

In the body movement detection sensor, the elastic sheet may be provided so as to be positioned within a range in front of a chest region.

The body movement detection sensor may include a circuit section having a function of measuring breathing, heartbeat, or body movements.

Advantageous Effects of Invention

According to the present invention, it becomes possible to provide a body movement detection sensor using a piezoelectric film, which has high detection accuracy with a structure that allows for size reduction.

DESCRIPTION OF EMBODIMENTS

A body movement detection sensor 1 according to an embodiment example will now be described with reference to the drawings.

<Configuration>

Figure 1:
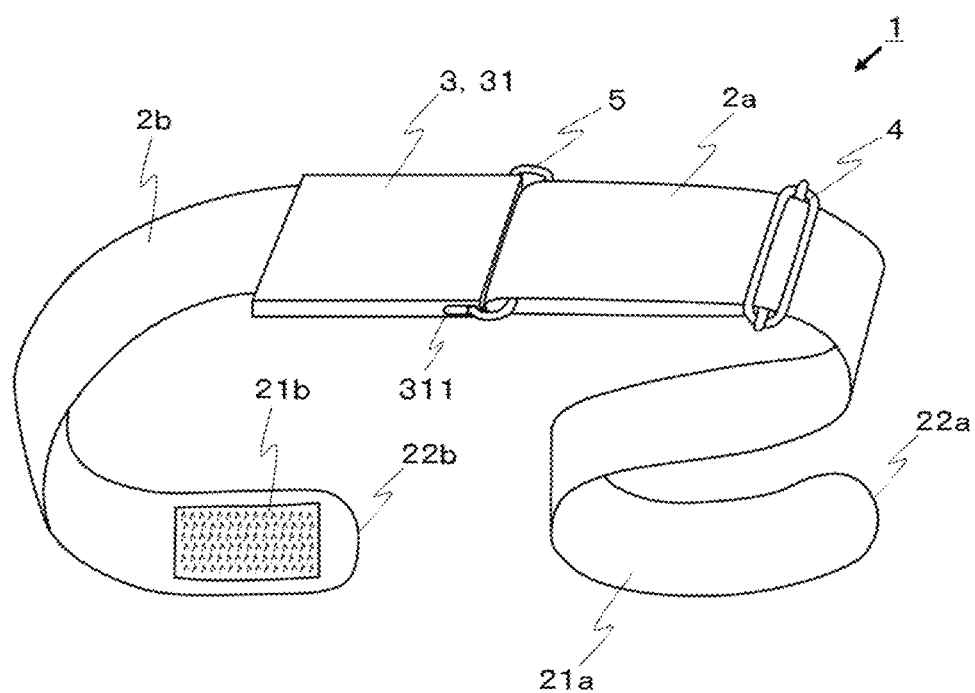
FIG. 1 is a configuration diagram of a body movement detection sensor according to an embodiment example.

As shown in FIG. 1, the body movement detection sensor 1 according to the embodiment example includes belt members 2, a sensor section 3, a slide member 4, and an annular part 5. This body movement detection sensor 1 is worn on a chest region of a person to be measured for use in monitoring presence or absence of breathing.

The belt members 2a and 2b are formed of material having substantially no elasticity (for example, high density chemical fiber fabric) and have a length adjustable by the slide member 4 and hook-and-loop fasteners 21a and 21b. An end portion of the belt member 2a at the side of the sensor section 3 is coupled to the slide member 4. Between the slide member 4 and the annular part 5, the belt member 2a is arranged so as to be inserted through the annular part 5 and doubled back over the belt member 2a. In the vicinity of an open-end portion 22b of the belt member 2b, a male hook-and-loop fastener 21b is provided, which can engage with a female hook-and-loop fastener 21a formed on the surface of the belt member 2a. Instead of the hook-and-loop fasteners 21a and 21b of the embodiment example, an engagement member that engages open-end portions (22a and 22b) of the belt members (2a and 2b) with each other may be configured, which can be an instrument such as a buckle.

Figure 2:
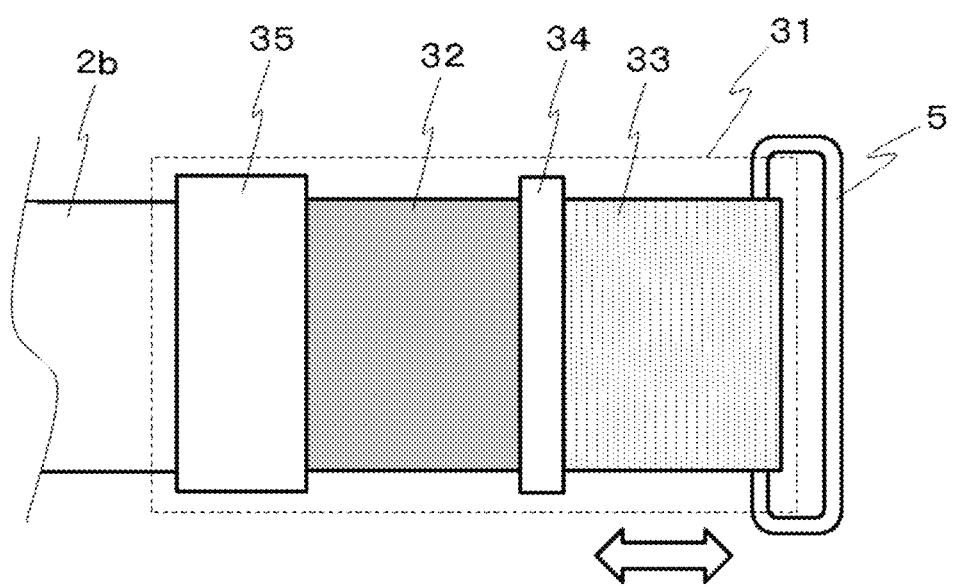
FIG. 2 is a plan view of a main part of a sensor section according to the embodiment example.

As shown in FIG. 2, the sensor section 3 includes a piezoelectric film 32, an elastic sheet 33, a coupling part 34, and a circuit section 35 that are housed in a case 31 made of resin or metal. Since the piezoelectric film 32 and the elastic sheet 33 that are housed in the case 31 are arranged so as to constitute a part of the belt without deflection (i.e., substantially without irregularities when viewed from a side), the case 31 is allowed for reduction of the thickness of the case 31. On both sides of the case 31, a pair of holes for movability 311 are formed through which the annular part 5 is inserted, which makes the annular part 5 slidable in the length direction along with expansions and contractions of the elastic sheet 33.

The piezoelectric film 32, which is a member in the shape of a film having substantially the same width as those of the belt members 2 or a narrower width compared to those of the belt members 2, has one end portion coupled to the coupling part 34 and the other end portion coupled to the circuit section 35.

The piezoelectric film 32 is whatever exhibits stronger piezoelectric effect in the length direction (an arrow direction in FIG. 2) than that in the width direction (a direction orthogonal to the arrow direction in FIG. 2). As the piezoelectric film 32, for example, Polyvinylidene fluoride film (PVDF) or piezoelectric ceramic or a piezoelectric ceramic thin film made of barium titanate, lead zirconate titanate (PZT), or the like is exemplified. Alternatively, fine powder of inorganic piezoelectric material may be used such as Pb (Zr.Ti) $O_3$, $PbTiO_3$, and (Pb, La) (ZR, Ti) $O_3$ dispersed in polymer material such as thermoplastic resin or thermosetting resin. Among them, PVDF is preferable since it is characterized by lightness, rich flexibility, a large response band, and hardly having specific resonance frequencies. The piezoelectric film 32 may be shielded by conductive cloth tape against noise.

Note that the piezoelectric film 32 may be configured with a plurality of piezoelectric films arranged in parallel alignment.

The elastic sheet 33 is an elastic member (for example, rubber sheet or rubber band) having substantially the same width as those of the belt members 2 or the piezoelectric film 32. The elastic sheet 33 has one end portion coupled to the coupling part 34 and the other end portion coupled to the annular part 5. The elastic sheet 33 is sufficiently shorter than the belt members 2 so that tension change of the elastic sheet 33 can directly affects the piezoelectric film 32. In an aspect, little amount of expansion of the elastic sheet 33 would impede breathing movements of a wearer and, thus, the elastic sheet 33 requires a certain length. How long the elastic sheet 33 is to be also depends on selection of material of the elastic sheet 33, but it needs to be taken into account that, unless at least a maximum amount of expansion of the elastic sheet 33 is set to be larger than an amount of change of a thorax during breathing, breathing movements of the wearer are encumbered. In another aspect, if the length of the elastic sheet 33 is equal to or larger than a certain length, it is considered that tension of the elastic sheet 33 is not sufficiently transmitted to the piezoelectric film 32 due to friction of clothes and the like and, particularly, that this problem becomes predominant in a case where the elastic sheet 33 is positioned in a side trunk region where the curvature changes. Accordingly, it is disclosed that the length of the elastic sheet 33 preferably falls within a range in front (or back) of the chest region, which is, for example, equal to or smaller than one-sixth (preferably one-eighth or more preferably one-tenth) of the total length of the belt members 2.

Note that the elastic sheet 33 may be configured with a plurality of elastic sheets arranged in parallel alignment.

The length of the elastic sheet 33 is examined.

In a case of adults, a general amount of change of a thorax during breathing is 30 to 60 mm. When the elastic sheet 33 is formed of knitted rubber, which can expand about twice in the length direction, it is disclosed that the length of the elastic sheet 33 has to be at least 30 to 60 mm and it is 60 to 120 mm when considering a margin. Herein, according to a standard of underwear of a certain manufacturer, a standard chest perimeter of males is 78 to 136 cm and a standard chest perimeter of females is 74 to 110 cm and, thus, the length of 60 mm represents 4.41 to 7.69% of the standard chest perimeter of males and 5.45 to 8.11% of the standard chest perimeter of females.

In a case of infants, a general amount of change of a thorax during breathing is 5 to 10 mm. When the elastic sheet 33 is formed of knitted rubber, which can expand about twice in the length direction, it is disclosed that the length of the elastic sheet 33 has to be at least 5 to 10 mm and it is 10 to 20 mm when considering a margin. Herein, a standard chest perimeter of infants of a certain manufacturer is 29 to 35 cm and thus the length of 10 mm represents 2.86 to 3.45% of the standard chest perimeter of infants. In the case of infants, in order to avoid unexpected accidents, the length of the elastic sheet 33 is preferably designed with a margin.

In a case where the amount of change of the thorax during breathing and the maximum amount of expansion of the elastic sheet 33 is coincident, tension change which is optimum to generate electric voltage in the piezoelectric film 32 can be obtained. However, since there are individual differences in an amount of change of a thorax during breathing, having a certain amount of allowance is also required.

Thus, it is considered preferable to employ the elastic sheet 33 of which maximum amount of expansion is one to two times as large as the general amount of change of a thorax during breathing and of which length is equal to or smaller than one-sixth (preferably one-eighth or more preferably one-tenth) of the total length of the belt members 2. Specifically, it is disclosed to employ the elastic sheet 33 of which length leads to the maximum amount of expansion being 30 to 120 mm in the case of adults, 10 to 30 mm in the case of infants, or 20 to 60 mm in the case of children.

The circuit section 35 includes an electrode electrically connected to a terminal of the piezoelectric film 32 and an output terminal to send out electric signals to a measurement circuit such as a charge amplifier or a field drop transistor (FET). The circuit section 35 may be provided with the measurement circuit and a micro-computer with a function of measuring breathing, heartbeat, or body movements. Even when a chest perimeter is varied by breathing, the circuit section 35 of the embodiment example will not move since it is fixed to the case 31.

The slide member 4, which is a member in the shape of "8" of a seven-segment display, is made of metal or resin, for example. Shifting a position of the slide member 4 allows the length of the belt member 2a to be adjusted.

The annular part 5, which is slidably inserted through end portions of the sides of the case 31, is made of metal or resin, for example. Slide movements of the annular part 5 in the length direction in the holes for movability 311 and 311 results in tension change of the elastic sheet 33. Note that the annular part 5 is not necessarily continuous and a notch may be formed thereon at the side of the belt member 2a or the side of the elastic sheet 33.

In the embodiment example, a configuration is employed that allows an end portion of the elastic sheet 33 at the side of the belt member 2a to be shifted. Alternatively to this, however, a configuration may be employed that fixes the end portion of the elastic sheet 33 at the side of the belt member 2a or fixes a member coupled to that end portion unslidably and that allows an end portion of the elastic sheet 33 at the side of the belt member 2b to be shifted (for example, a configuration that unslidably fixes the annular part 5 and that makes the circuit section 35 slidable in the case 31). In this case, the slide member 4 and the annular part 5 are not indispensable configuration elements and, for example, the belt member 2a and the elastic sheet 33 may be directly coupled to each other.

<Measurement Principle>

Measurement principle of the body movement detection sensor 1 will be described with reference to FIGS. 3A and 3B.

The body movement detection sensor 1 converts change in a perimeter of the thorax to tension of the elastic sheet 33, which causes voltage change of the piezoelectric sensor 32. Herein, it is important to combine the non-elastic belt members 2 with the elastic sheet 33 which is sufficiently shorter compared to the belt members 2 and to thereby apply tension being equal to or larger than a certain level to the piezoelectric film 32 in the length direction.

Figures 3A, 3B:
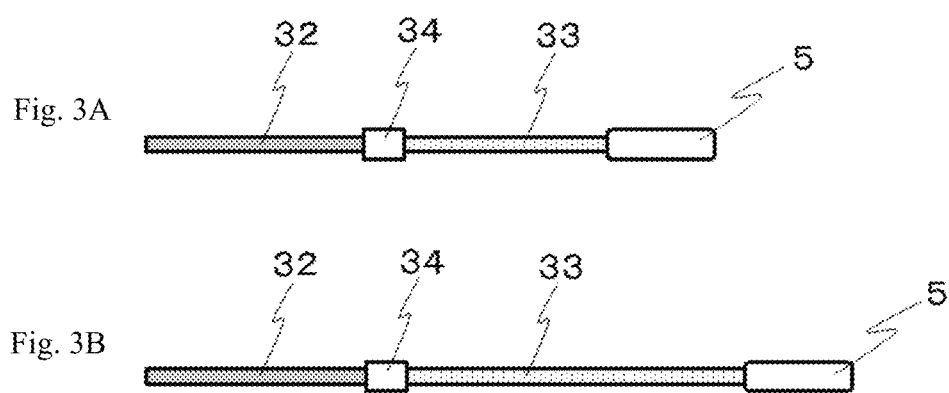
FIGS. 3A and 3B show side views of the main part illustrating a measurement principle of the body movement detection sensor according to the embodiment example, with FIG. 3A showing an exhaled state and FIG. 3B showing an inhaled state.

FIG. 3A is a diagram showing an expansion state of the elastic sheet 33 in an exhaled state of the person to be measured. In this state, expansion of the elastic sheet 33 is small and thus tension change applied to the piezoelectric film 32 is also small, which causes small electric voltage.

FIG. 3B is a diagram showing an expansion state of the elastic sheet 33 in an inhaled state of the person to be measured. In this state, the expansion of the elastic sheet 33 is large and thus the tension change applied to the piezoelectric film 32 is also large, which causes large electric voltage.

Note that the expansion of the piezoelectric film 32 caused by pulling is marginal.

<Measurement Experiments>

An experiment of measuring breathing was conducted with a piezo film of TOKYO SENSOR CO., LTD. (DT2-028) employed for the piezoelectric film 32 of the body movement detection sensor 1, Promark training band level 1 of SAKURAI CO., LTD. (TPT0077) employed for the elastic sheet 33, and a charge amplifier and a preamplifier used. The piezoelectric film 32 had a width of 16 mm and a length of 73 mm. The elastic sheet 33, of which material was natural latex rubber, had a width of 150 mm and a length of 50 mm.

Figure 4A:
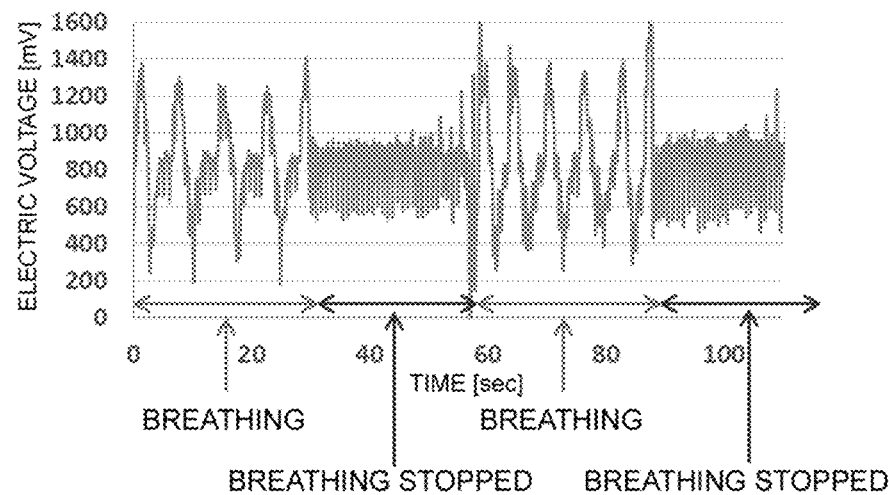
FIG. 4A is data showing a measurement result of the body movement detection sensor according to the embodiment example.
Figure 4B:
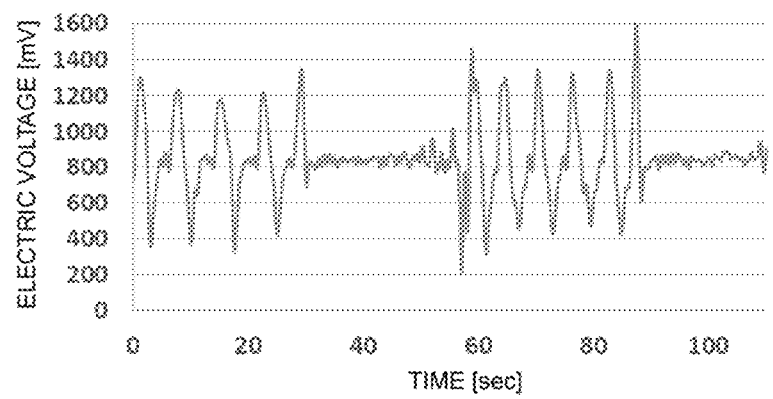
FIG. 4B is a graph of breathing data obtained by processing the data of FIG. 4A.
Figure 4C:
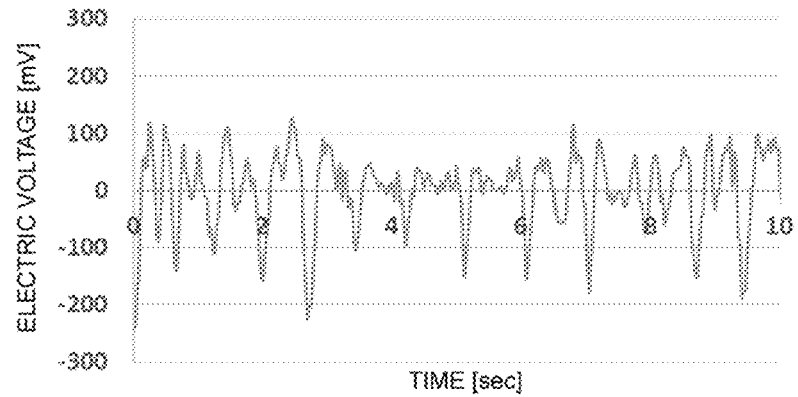
FIG. 4C is a graph of heartbeat data obtained by processing the data of FIG. 4A.

FIG. 4A is data showing a measurement result of the body movement detection sensor 1, FIG. 4B is a graph of breathing data obtained by applying 0.2 Hz low-pass digital filter processing to the data of FIG. 4A, and FIG. 4C is a graph of heartbeat data obtained by applying 1 Hz high-pass digital filter processing to the data of FIG. 4A.

Figure 5:
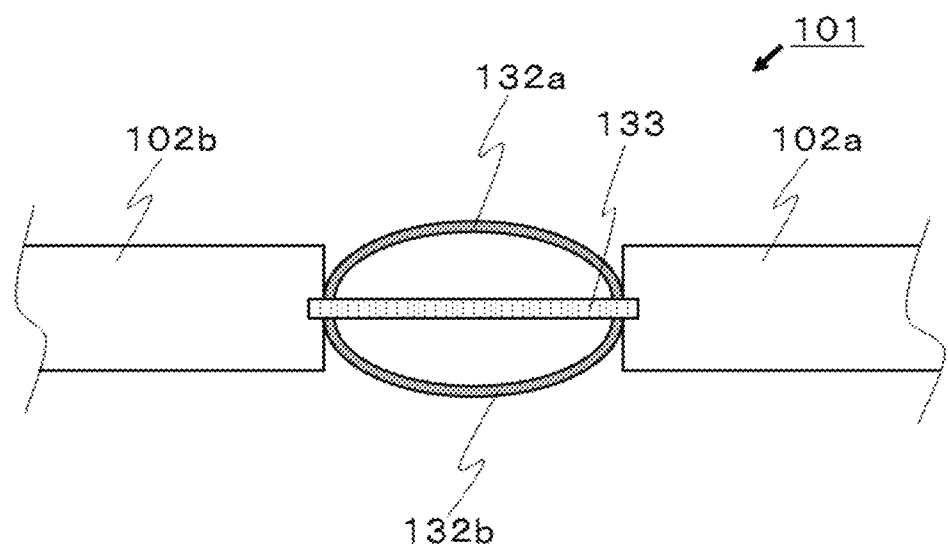
FIG. 5 is a plan view of a body movement detection sensor according to a comparative example.

FIG. 5 is a plan view of a body movement detection sensor 101 according to a comparative example disclosed in Patent Literature 2, where piezoelectric films of the body movement detection sensor were duplicated. The body movement detection sensor 101 according to the comparative example included non-elastic belts 102a and 102b, piezoelectric films 132a and 132b, and an elastic sheet 133.

The piezoelectric films 132a and 132b, which were deflected in the shape of a bridge, were symmetrically arranged with respect to the elastic sheet 133. LDT2-028K/L of TOKYO SENSOR CO., LTD was employed for each of the piezoelectric films 132a and 132b. Promark training band level 1 of SAKURAI CO., LTD. (TPT0077) mentioned above was employed for the elastic sheet 133, of which both end portions are respectively coupled to the belts 102a and 102b. The body movement detection sensor shown in FIG. 5 was used to conduct an experiment of measuring breathing of adults by using a charge amplifier and a preamplifier.

Figure 6A:
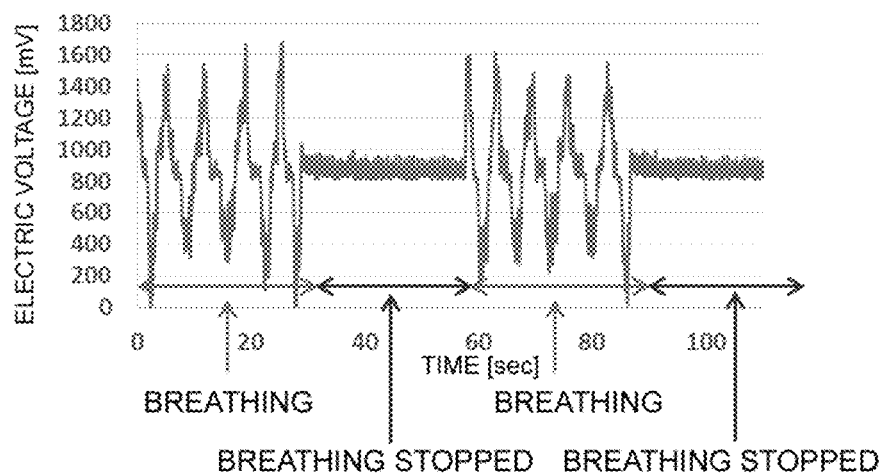
FIG. 6A is data showing a measurement result of the body movement detection sensor according to the comparative example.
Figure 6B:
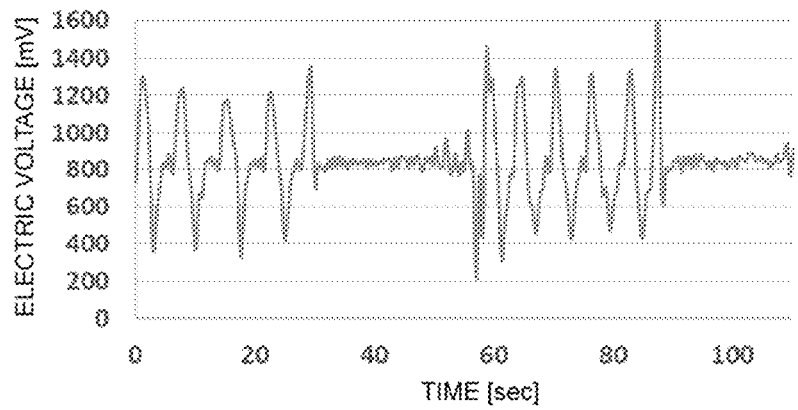
FIG. 6B is a graph of breathing data obtained by processing the data of FIG. 6A.
Figure 6C:
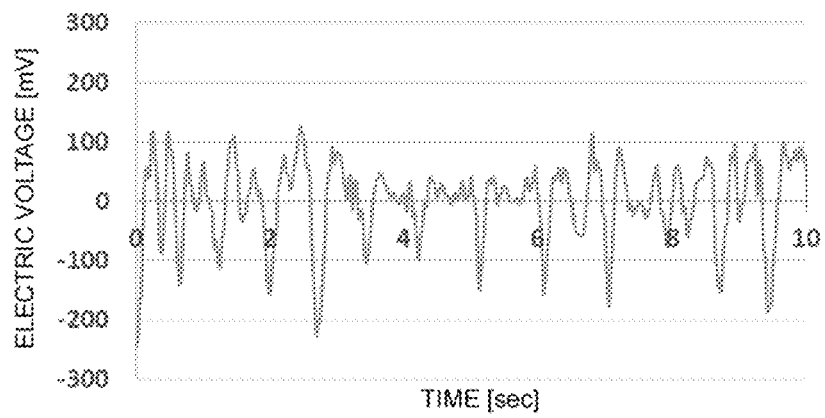
FIG. 6C is a graph of heartbeat data obtained by processing the data of FIG. 6A.

FIG. 6A is data showing a measurement result of the body movement detection sensor 101 according to the comparative example, FIG. 6B is a graph of breathing data obtained by applying 0.2 Hz low-pass digital filter processing to the data of FIG. 6A, and FIG. 6C is a graph of heartbeat data obtained by applying 1 Hz high-pass digital filter processing to the data of FIG. 6A.

As can be seen by comparison between FIGS. 4A to 4C and FIGS. 6A to 6C, it was confirmed that both of the body movement detection sensors 1 and 101 measured breathing data with high accuracy. However, the embodiment example where the piezoelectric film does not have to be deflected is superior in that the size of the sensor section can be considerably reduced in volume. Furthermore, the body movement detection sensor 101 of the comparative example can have high sensitivity for detecting body movements only within a gap from the length at which the deflected piezoelectric film 132a is straightened to the length at which the elastic sheet 133 is contracted. Hence, in order to detect body movements of adults, a gap of, for example, about 30 mm to 60 mm is required, which highly increases the thickness. In contrast, as for the body movement detection sensor 1 of the embodiment example, just adjusting the length of the elastic sheet 33 is required even if an amount of change in a perimeter of a thorax for detecting body movements of adults is, for example, about 30 mm to 60 mm. This will remove a need to increase the thickness. The characteristics of allowing for reduction in thickness is highly useful particularly in a case of application of the body movement detection sensor to infants and the like.

The preferred embodiment of the present invention is described above. However, the technical scope of the present invention is not limited to the description of the above embodiment. Various alterations and improvements can be applied to the above embodiment and such altered or improved modes are also within the technical scope of the present invention.

Figure 7A:
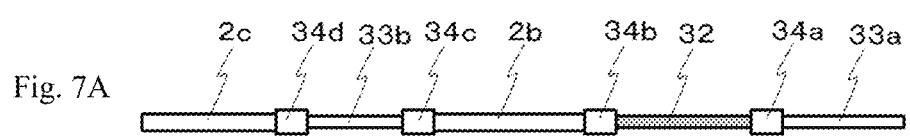
FIG. 7A shows a side view of a main part of a body movement detection sensor according to each alteration example.
Figure 7B:
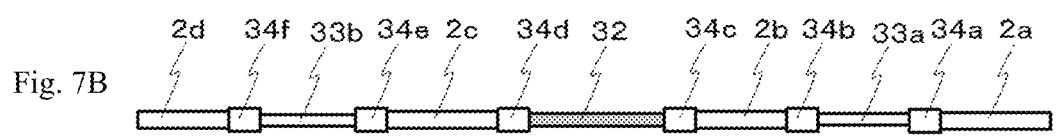
FIG. 7B shows a side view of a main part of a body movement detection sensor according to each alteration example.

For example, it is disclosed that an elastic sheet 33b may be arranged in the middle of belt members (2b and 2c) at the left side of a piezoelectric film 32 as shown in FIG. 7A and that two elastic sheets (33a and 33b) may be coupled to each other via two belt members (2b and 2c) arranged on the respective sides of a piezoelectric film 32 as shown in FIG. 7B. In this case, it is important that a total amount of expansion of the two elastic sheets (33a and 33b) is set to be similar to the amount of expansion in the case of the above configuration having one elastic sheet (in the case of adults, 30 to 120 mm).

Additionally, the elastic sheet is preferably arranged as close as possible to the piezoelectric film 32 since sensitivity may drop due to friction of clothes and the like.

Note that FIGS. 7A and 7B show schematic diagrams and the length of each member is not exactly depicted. The same reference signs are added to similar configuration elements to those of the embodiment example and descriptions thereof are omitted.

INDUSTRIAL APPLICABILITY

The present invention is applicable to a scene wherever it is used for the purpose of vibration detection under circumstances of temperature change. As specific examples, there are applications in a switch of a dust-proof mask with an electromagnetic valve, in monitoring breathing of a person on a population respirator, in treatment at home with an artificial respirator for a muscular dystrophy patient, in a sleep detection system monitoring a breathing state of a vehicle driver, and in monitoring delivery timing of humans or animals.

The invention claimed is:
1. A body movement detection sensor comprising:
a sensor section having a non-elastic piezoelectric film and to be worn on a chest region;
a right belt member extending from a right side of the sensor section;
a left belt member extending from a left side of the sensor section; and
an engagement member for engaging an end portion of the right belt member and an open-end portion of the left belt member with each other;
wherein the piezoelectric film exhibits piezoelectric effect in a length direction,
the right belt member and the left belt member have substantially no elasticity,
the body movement detection sensor further comprises an elastic sheet directly or indirectly connected to the right belt member and the left belt member,
the piezoelectric film and the elastic sheet are arranged substantially without irregularities when viewed from a side,
the elastic sheet has a maximum amount of expansion larger than an amount of change of a thorax during breathing, has a length equal to or smaller than one-sixth of a total length of the right belt member and the left belt member, and is arranged so as to be within a range in front or back of the chest region of a wearer,
the sensor section comprises a case covering the piezoelectric film and the elastic sheet, and
the case comprises a pair of holes for movability disposed on sides of the case, the body movement detection sensor comprises an annular part slidably inserted through the pair of holes for movability, and the elastic sheet arranged in the case is coupled to the right belt member or the left belt member via the annular part.

2. The body movement detection sensor according to claim 1, wherein the elastic sheet has:
a maximum amount of expansion of 30 to 120 mm for adults;
a maximum amount of expansion of 10 to 20 mm for infants; or
a maximum amount of expansion of 20 to 60 mm for children.

3. The body movement detection sensor according to claim 1, further comprising a slide member that makes a length of the right belt member and/or the left belt member adjustable.

4. The body movement detection sensor according to claim 1, comprising a circuit section fixed and arranged in the case, the circuit section having a function of measuring breathing, heartbeat, or body movements.

5. The body movement detection sensor according to claim 1, comprising a circuit section arranged so as to be slidable in the case, the circuit section having a function of measuring breathing, heartbeat, or body movements.

6. The body movement detection sensor according to claim 1, wherein the elastic sheet consists of a plurality of elastic sheets arranged so as to hold the piezoelectric film between the elastic sheets.

\* \* \* \* \*